United States Patent [19]
Myers

[11] Patent Number: 5,578,301
[45] Date of Patent: Nov. 26, 1996

[54] METHOD FOR USING GM-CSF TO REDUCE THE ACUTE PHASE RESPONSE IN A PATIENT BEING ADMINISTERED IL-6 THERAPY

[75] Inventor: Laurie A. Myers, Morris Plains, N.J.

[73] Assignee: Sandoz Ltd., Basel, Switzerland

[21] Appl. No.: 167,253

[22] Filed: Dec. 14, 1993

[51] Int. Cl.$^6$ ..................................................... A61K 45/05
[52] U.S. Cl. ......................................... 424/85.1; 424/85.2
[58] Field of Search .................................... 424/85.1, 85.2

[56] References Cited

U.S. PATENT DOCUMENTS

| | | | |
|---|---|---|---|
| 5,171,840 | 12/1992 | Kishimoto | 530/350 |
| 5,178,856 | 1/1993 | Burstein | 424/85.2 |
| 5,188,828 | 2/1993 | Goldberg et al. | 424/85.2 |
| 5,229,496 | 7/1993 | Deeley et al. | 530/351 |

FOREIGN PATENT DOCUMENTS

| | | |
|---|---|---|
| 0378171 | 7/1990 | European Pat. Off. . |
| 3027320 | 6/1989 | Japan . |
| 8600639 | 1/1986 | WIPO . |
| 8800206 | 1/1988 | WIPO . |
| 9107988 | 6/1991 | WIPO . |

OTHER PUBLICATIONS

Chang et al., "Phase I Study of Interleukin–6 (IL–6) in Cancer Patients Treated with Ifosfamide, Carboplatin, and Etoposide (Ice)," Blood, 80, 1992 (No. 10, Suppl. 1) Abs. 346.
Demetri et al., "Recombinant Human Interleukin–6 (IL–6) Increases Circulating Platelet Counts and C–Reactive Protein Levels In Vivo: Initial Results of a Phase I Trial in Sarcoma Patients with Normal Hemopoiesis," Blood, 80 1992, (No. 10, Suppl. 1) Abs. 344.
Fay et al., "Concomitant Administration of Interleukin–6 (rH IL–6) and Leucomax (rh GM–SCF) Following Autologous Bone Marrow Transplantation–A Phase I Trial," Blood 1993, vol. 82, (10, Suppl. 1), p. 431a (abs. 1707).
Gasparetto et al., "Dyshematopoiesis in Combined Immune Deficiency with Congenital Neutropenia," Am. J. Hematol., (1994) 45/1 (63–72).
Gauldie et al., "Interferon B$_2$/B–cell stimulatory factor type 2 shares identity with monocyte–derived hepatocyte–stimulating factor and regulates the major acute phase protein response in liver cells," PNAS USA 84: 7251 (1987).
Geiger et al., "Induction of rat acute phase proteins by interleukin 6 in vivo," Eur. J. Immunol. 18: 717 (1988).
Harousseau et al., "Phase I/II trial of recombinant human IL–6 and GM–CSF following autologous bone marrow transplantation for non–Hodgkin's lymphoma," EBMT, Mar. 13, 1994 Harrowgate Meeting.
Heinrich et al., "Interleukin–6 and the acute phase response," Biochem. J. (1990) 265, 621–636.
Iguchi et al., "Effect of Recombinant Human Granulocyte Colony–Stimulating Factor Administration in Normal and Experimentally Infected Newborn Rats," Exp Hematol., (1991 Jun.) 19 (5), pp. 352–358.

Akira et al., "A Nuclear Factor for IL–6 Expression (NF–IL6) is a Member of a C/EBP Family," EMBO J, (1990 Jun.) 9 (6) 1897–1906.
Akira et al., "IL–6 and NF–IL6 in Acute Phase Response and Viral Infection," Immunol. Rev., (1992 Jun.) 127, 25–50.
Akira et al., "Interleukin–6 in Biology and Medicine," Adv. Immunol., (1993) 54, pp. 22–27.
Andus et al., "Recombinant human B cell stimulatory factor 2 (BSF–2/IFN–B2) regulates B–fibrinogen and albumin mRNA levels in Fao–9 cells," FEBS Lett. 221:18 (1987).
Bataille et al., "Cytokines et Proliferations Lymphoplasmocytaires: Role Essential de L'Interleukine 6", Rev Prat (Paris) 1993, 43, 3, pp. 275–278.
Caracciolo et al., "Human Interleukin–6 Supports Granulocytic Differentiation of Hematopoietic Progenitor Cells and Acts Synergistically with GM–CSF," Blood, vol. 73, No. 3, (Feb. 15), 1989: 666–670.
Castell et al., "Recombinant human interleukin–6 (IL–6/BSF–2/HSF) regulates the synthesis of acute phase proteins in human hepatocytes," FEBS Lett. 232:347 (1988).
Castell et al., "Interleukin–6. The Major Regulator of Acute–Phase Protein Synthesis in Man and Rat," 1989. Ann. N.Y. Acad. Sci., 557: 87–101.
Rennick et al., "Interleukin–6 Interacts with Interleukin–4 and Other Hematopoietic Growth Factors to Selectively Enhance the Growth of Megakaryocytic, Erythroid, Myeloid, and Multipotential Progenitor Cells," Blood, vol. 73, No. 7, (May 15), 1989, pp. 1828–1835.
Ryffel et al., "Pathology Induced by Interleukin–6," Toxicology Letters, 64/65, (1992) 311–319.
Sehgal, "Interleukin–6: Molecular Pathophysiology," J Invest Dermatol, 94 (Suppl): No. 6, pp. 2S–6S, (Jun. 1990).
Schipperus et al., "IL–6 enhances the GM–CSF induced in vitro colony formation of myelodysplastic marrow myeloid progenitor cells," Neth. J. Med., 37 (1990), p.A. 34.
Spronk et al., "Plasma concentration of IL–6 in systemic lupus erythematosus; an indicator of disease activity," Clin. exp. Immunol., (1992) 90, 106–110.
Stahl et al., "Effects of Human Interleukin–6 on Megakaryocyte Development and Thrombocytopoiesis in Primates," Blood, vol. 78, No. 6 (Sep. 15), 1991: pp. 1467–1475.
Swaak et al., "Interleukin–6(IL–6) and acute phase proteins in the disease course of patients with systemic lupus erythematosus," Rheumatol Int (1989) 8: 263–268.
Van Snick, "Interleukin–6: An Overview," Annu. Rev. Immunol. 1990, 8: 253–78.
Klein et al., "Interleukine 6 et myelome multiple chez l'homme" medicine/sciences 1991; 7: 937–43.

(List continued on next page.)

Primary Examiner—Chhaya D. Sayala
Attorney, Agent, or Firm—Robert S. Honor; Melvyn M. Kassenoff; Diane E. Furman

[57] ABSTRACT

A method for reducing or suppressing the acute phase response in a patient receiving IL-6 treatment which comprises co-administering with the IL-6 an effective amount of granulocyte macrophage colony stimulating factor (GM-CSF).

17 Claims, 7 Drawing Sheets

OTHER PUBLICATIONS

Kushner et al., "Acute Phase Proteins as Disease Markers," in *Disease Markers,* vol. 5, 1–11 (1987).

MacVittie et al., "Therapeutic Efficacy of rh IL-6 in a Nonhvman Primate Model of High Dose, Sublethal, Radiation-Induced Marrow Aplasia," Blood, 80 1992, (No. 10, Suppl 1), Abs. 347.

McDonald, "The Regulation of Megakaryocyte and Platelet Production," in *Concise Reviews in Clinical and Experimental Hematology,* ed. M. Murphy, AlphaMed Press, Dayton, Ohio (1992) at 161–178.

Metsarinne et al., "Plasma interleukin-6 and renin substrate in reactive arthritis, rheumatoid arthritis, and systemic lupus erythematosus," Rheumatol Int. (1992) 12: 93–96.

Nijsten et al., "Serum Levels of Interleukin-6 and Acute Phase Responses," Lancet ii:921 (1987).

Olencki et al., "Phase IA/IB Trial of rhIL-6 in Patients with Refractory Malignancy: Hematologic and Immunologic Effects," Blood, Nov. 15, 1992, vol. 80, No. 10, Suppl. 1 #344.

Patchen et al., "Administration of Interleukin-6 Stimulates Multilineage Hematopoiesis and Accelerates Recovery From Radiation-Induced Hematopoietic Depression," Blood, vol. 77, No. 3, (Feb. 1), 1991 pp. 472–480.

Patchen et al., "Effects of combined administration of interleukin-6 and granulocyte colony-stimulating factor on recovery from radiation-induced hemopoietic aplasia," Experimental Hematology, 21: 338–344 (1993).

Pepys, "Acute Phase Proteins," in *Encyclopedia of Immunology,* Roiitt, I, ed., Academic Press (1992), 16–18.

Tanikawa et al., Exp. Hematology, vol. 17, pp. 883–888, 1989.

Hamblin, "Cytokine and Cytokine Receptors," IRL Press, Chapter 4, 1993.

Gabrilove et al., J. Natl. Cancer Inst. Monogr., vol. 10, pp. 73–77, 1990.

Fibbe et al., Acta Haematol. (Basel), vol. 86(3), pp. 148–154, 1992.

Neta et al., Lymphokine Res., vol. 7(4), pp. 403–412, 1988.

Schaffner H, Allerg. Immunol., (Leipz.), vol. 36(2), pp. 77–86, 1990.

Akira et al., Adv. Immunol., vol. 54, pp. 1–78, 1993.

Ballou et al Adv. in Intern. Med. vol. 37 pp. 313–336 (1992).

Mayer et al Exp. Hematol. 19: 688–696 (1991).

METHOD FOR USING GM-CSF TO REDUCE THE ACUTE PHASE RESPONSE IN A PATIENT BEING ADMINISTERED IL-6 THERAPY

BACKGROUND

Hematopoiesis, the proliferation and differentiation of blood cells from pluripotent stem cells, has been found to be regulated by a variety of cell factors (i.e. cytokines), examples of which are the interleukins (IL's) and colony-stimulating factors (CSF's).

Human interleukin-6 (IL-6), in particular, is produced by the lymphoid and other cells and plays a role in stimulating proliferation of multiple lineages of hematopoietic cells. Examples of hematopoietic activities ascribed to IL-6 include antiviral activity, stimulation of B-cells and Ig secretion, induction of IL-2 and IL-2 receptor expression, enhancement of IL-3 induced colony formation, proliferation and differentiation of T-cells, maturation of megakaryocytes, and other functions.

The pleiotropic or multifunctional nature of human IL-6 is reflected in the plurality of names used in the art [e.g., interferon-$\beta_2$ (IFN$\beta_2$), 26 kDa protein (26 K), B-cell stimulatory factor 2 (BSF-2), hybridoma/plasmacytoma growth factor (HPGF), hepatocyte stimulating factor (HSF), cytotoxic T-cell differentiation factor (CDF)] to refer to what has been confirmed by molecular cloning to be a single protein of 212 amino acids and a molecular mass ranging from 21 to 28 kd, depending on the cellular source and preparation (see Van Snick, Ann. Rev. Immunol. 1990, 253. Recombinant human IL-6 protein has been molecularly cloned and purified to homogeneity.

Accordingly, the terms "IL-6" and "IL-6 protein" as used herein shall be understood to refer to a natural or recombinantly prepared protein, which may be glycosylated or unglycosylated and which has the amino acid sequence of natural human IL-6 as disclosed, for example, in published PCT application Serial No. WO 88/00206, which is incorporated herein by reference.

A well-documented inter-species activity of human IL-6 comprises stimulation of thrombocytopoiesis, i.e. the process by which megakaryocyte progenitor cells mature into megakaryocytes, from which the platelets are ultimately released into peripheral circulation (see McDonald, "The Regulation of Megakaryocyte and Platelet Production," in *Concise Reviews in Clinical and Experimental Hematology*, ed. by M. Murphy, AlphaMed Press, Dayton, Ohio (1992) at 167).

For example, administration of recombinant human IL-6 protein (hereinafter also "rhIL-6") to normal mice and monkeys has been found to result in increased megakaryocyte size and elevated peripheral blood platelet counts (see, e.g., Stahl et al., *Blood*, Vol. 78, No. 6, Sep. 15, 1991: pp 1467–1475; Mayer et al. Exp. Hematol. 19:688–696).

IL-6 induced platelet production has also been documented in a non-human primate model of radiation-induced marrow aplasia (see, e.g., Mackittie et al., *Blood*, Nov. 15, 1992, Vol. 80, No. 10), as well as in humans subjected to ICE chemotherapy, Chang et al., *Blood*, id.

The platelets contribute a vital homeostatic function by adhering and coagulating on damaged tissue and by secreting factors which initiate coagulation reactions. A deficiency of platelets (thrombocytopenia) whether caused by failure of platelet production (e.g., as a result of aplastic anemia), and/or megakaryocyte depression brought on by iatrogenic drugs, chemicals or viral infections, AIDS related problems and/or platelet destruction (e.g., as a result of secondary thrombocytopenia), can be a life-threatening condition, for which the only conventional treatments have been repeated platelet transfusions, or bone marrow transplantation, both involving risks of infection and rejection.

Administration of IL-6 to a patient suffering from platelet deficiency may therefore be practiced as an endogenous means of accelerating recovery from thrombocytopenia, and even spare the need for transfusion or transplantation. IL-6 may also be used and particularly important in treating subjects in whom thrombocytopenia has been induced by irradiation or administration of drugs which interfere with hematopoiesis (see Patchen et al., *Blood*, Vol. 77, No. 3 (February 1), 1991: pp. 472–480).

However, administration of IL-6 therapy to a mammalian patient for purposes of obtaining the various benefits and advantages therefrom, including, in particular, stimulation of thrombocytopoiesis, or for other therapeutic purposes, is often accompanied by associated systemic changes which may interfere with attainment of the therapeutic goal.

For example, IL-6 administration has been linked to certain responses by the liver which otherwise typically characterize the mammalian "acute phase response" to a challenge such as inflammation or tissue injury. Symptoms of the acute phase response include alteration in plasma protein levels and steroid concentrations, leukocytosis, increased vascular permeability, fever, patient malaise, discomfort, fatigue, weight loss and pallor (Andus et al., FEBS Lett. 221:18 (1987)).

In particular, IL-6 has been found to act on the hepatocytes to regulate production therein of certain plasma proteins typically associated with the acute phase response, which are referred to as "acute phase proteins," see Gauldie et al., PNAS USA 84: 7251 (1987); Geiger et al., *Eur. J. Immunol.* 18:717 (1988)).

Such acute phase proteins include both "up-regulated" proteins, plasma levels of which are increased in response to IL-6 administration, and "down-regulated" proteins, plasma levels of which are depressed by IL-6 (see Pepys, "Acute Phase Proteins," in *Encyclopedia of Immunology*, Roitt, I., ed., Academic Press (1992), 16–18).

Examples of "up-regulated" acute phase proteins include $a_1$-antitrypsin, haptoglobulin, ceruloplasmin, alpha-1-acid glycoprotein, C-reactive protein (CRP), and alpha-2-macroglobulin. An example of a "down-regulated" protein comprises prealbumin (see Mayer et al., *Exp. Hematol.* 19:688–696 (1991)).

The extent of an acute phase response accompanying in vivo administration of IL-6 can be correlated to measurable changes in the serum levels of such circulating acute phase proteins.

Studies in normal rhesus monkeys demonstrate that IL-6 administration may be accompanied by a dose-related increase in serum levels of positively regulated acute phase proteins, such as CRP, alpha-1-glycoprotein, gamma-globulin, $\alpha$-2-macroglobulin and fibrinogen, and likewise, a dose-related decrease in negatively regulated prealbumin, Mayer et al., id.; Ryffel et al., *Toxicoloqy Letters*, 64/65 (1992), 311–319. See also Geiger et al., *Eur. J. Immunol.* 18:717 (1988); Castell et al., *FEBS Lett.* 232:347 (1988); Nijstein et al., *Lancet* ii:921 (1987). In Phase I trials of rhIL-6 in human cancer patients, acute phase proteins including CRP and fibrinogen increased during therapy. Olencki et al., *Blood*, Nov. 15, 1992, Vol. 80, No. 10, Supp. 1, #344, 346.

The occurrence of associated systemic changes comprising an acute phase response in patients receiving IL-6 therapy can result in patient discomfort, and even become pathologic, to the point where the patient's tolerability to a drug becomes in question. A means of reducing an acute phase response can significantly improve the overall practical utility of therapeutic substances indicated to produce such response.

Granulocyte macrophage colony stimulating factor (GM-CSF) has been shown to exert a regulatory effect on granulocyte-committed progenitor cells to increase circulating granulocyte levels. In particular, GM-CSF acts as a growth factor for granulocyte, monocyte and eosinophil progenitors. Administration of GM-CSF in human and non-human primates results in increased numbers of circulating neutrophils, as well as eosinophils, monocytes and lymphocytes. Accordingly, GM-CSF can be particularly useful in accelerating recovery from neutropenia in patients subjected to radiation or chemotherapy, or following bone marrow transplantation.

Human GM-CSF (hGM-CSF) has also been isolated and cloned, see published International Application No. PCT/EP 85/00326, filed Jul. 4, 1985 (published as WO 86/00639).

The term "GM-CSF" as used herein shall be understood to refer to a natural or recombinantly prepared protein having substantial identity to an amino acid sequence of human GM-CSF as disclosed, for example, in published international application WO 86/00639, which is incorporated herein by reference. Recombinant human GM-CSF is hereinafter also referred to as "rhGM-CSF".

SUMMARY OF THE INVENTION

It has now been found that an acute phase response in a patient receiving IL-6 can be reduced or suppressed by co-administering GM-CSF with the IL-6.

In particular, it has been found that co-administration of at least an equal weight amount of GM-CSF with IL-6 can reduce IL-6-mediated changes in circulating levels of acute phase proteins.

These observations support the conclusion that GM-CSF, when co-administered in the indicated minimum ratio acts synergistically or in an unknown and unpredictable way to suppress aspects of the acute phase response, without foregoing certain primary therapeutic utilities of IL-6, e.g., thrombocytopoiesis and without lessening the neutrophil stimulation which may be provided by GM-CSF when also given in an amount to effect such stimulation.

There appears to be no prior recognition in the art that GM-CSF may be co-administered with IL-6 to reduce or suppress the acute phase response.

The present invention therefore comprises a method for reducing the acute phase response in a patient receiving IL-6, which method comprises co-administering an acute phase protein-reducing effective amount of GM-CSF with the IL-6.

The invention also provides therapeutic compositions to be administered in accordance with the method of the invention.

Patients to be treated by the method of the invention include mammals, including human and non-human primates, especially humans.

BRIEF DESCRIPTION OF THE DRAWINGS

FIG. 1 depicts changes in the average platelet count of each group from baseline levels;

FIG. 2 depicts the change in average neutrophil level of each group from baseline levels;

FIG. 3 is a bar graph representing the change in average erythrocyte sedimentation rate (ESR);

FIG. 4 is a bar graph showing the baseline average serum $\alpha$-2-macroglobulin level for each group prior to cytokine administration;

FIG. 5 shows the average serum $\alpha$-2-macroglobulin level following administration of cytokine;

FIG. 6 is a bar graph showing the average baseline serum fibrinogen level for each group prior to cytokine administration;

FIG. 7 is a bar graph showing the average fibrinogen level for each group;

DETAILED DESCRIPTION

Figure 1:
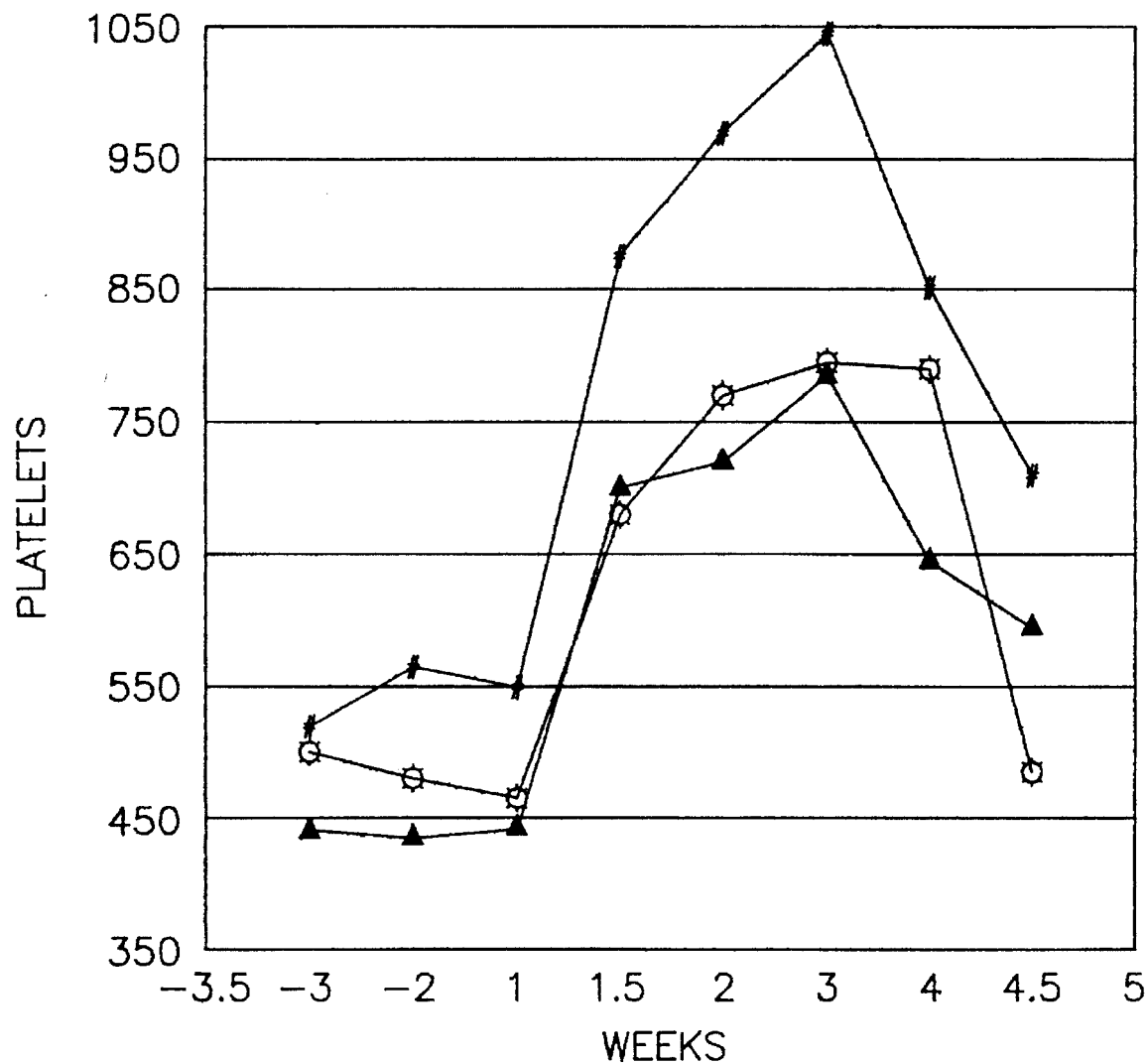
FIGS. 1–7 comprise a series of graphs which demonstrate the effect on various aspects of the acute phase response of administering to rhesus monkeys a course of therapy comprising either of: rhIL-6 (Group I); rhGM-CSF (Group II); or rhIL-6 and rhGM-CSF (Group IV).

The human IL-6 used in the present invention may be purified from natural sources or produced by recombinant means, as is well-known. GM-CSF can also be similarly obtained. Preferably, the cytokines are obtained by culturing transformants obtained by transforming a host with recombinant DNA comprising at least the human cDNA under the control of a suitable promoter. Preferred methods of recombinantly producing mammalian IL-6 and GM-CSF involve expression in bacteria or yeast cells, although recombinant proteins can also be produced using mammalian cells, insect cells, or other cells under the control of appropriate promoters.

The proteins can be glycosylated to varying degrees or unglycosylated.

*E. coli* derived, non-glycosylated rhIL-6 can be obtained by the methods described in published PCT Application WO 88/00206, or can be glycosylated, mammalian cell-produced IL-6 as described therein.

*E. coli* derived, non-glycosylated rhGM-CSF can be obtained by the methods described in publication of the International Application No. PCT/EP 85/00326, wherein two native GM-CSFs differing in a single amino acid are described.

The natural human IL-6 and GM-CSF proteins used in the invention may be modified by changing the amino acid sequence thereof. For example, from 1 to 5 amino acids in their sequences may be changed, or their sequences may be lengthened, without changing the fundamental character thereof and provide modified proteins which are the full functional equivalents of the native proteins. Such functional equivalents may also be used in practicing the present invention. A GM-CSF differing by a single amino acid from the common native sequence is disclosed in U.S. Pat. No. 5,229,496 and has been produced in glycosylated form in yeast, and has been clinically demonstrated to be a biological equivalent of native GM-CSF, such modified form known as GM-CSF (Leu-23).

The natural or recombinantly prepared proteins, and their functional equivalents used in the method of the invention are preferably purified and substantially cell-free, which may be accomplished by known procedures.

According to the method of the invention, reduction or suppression of the acute phase response in a patient receiving IL-6 therapy can be effectuated by co-administering to the patient an amount of GM-CSF which is equal to or greater than the amount of the IL-6, the amount of each being expressed as unglycosylated protein.

As previously indicated, the extent of an acute phase response in a patient receiving IL-6 can be reasonably correlated to changes in serum levels of certain acute phase proteins, in particular, CRP, α-2-macroglobulin and fibrinogen.

Therefore, the extent of an acute phase response in a subject being administered IL-6 can be determined based on the difference between the baseline serum level of one or more circulating acute phase proteins, i.e. the level prior to initial administration of IL-6, and the serum level of the protein following commencement of IL-6 administration.

The unexpected effect of GM-CSF co-administration with the IL-6 can be estimated by comparing the serum level of one or more acute phase proteins taken after initial administration of IL-6 alone, with the serum level taken after GM-CSF is co-administered with IL-6.

Baseline levels of protein may be measured any time prior to IL-6 administration, preferably within 3–4 weeks, and more preferably within 2 weeks or 1 week, prior to the IL-6 therapy.

Post-administration protein levels are preferably determined after four days of administration and within 24 hours of IL-6 dosing. Preferably, serum samples are taken before the IL-6 is completely metabolized, most preferably within 6 hours of IL-6 administration to the patient. Periodic monitoring, every 3–7 days, will take place over the longer treatment periods, and upon completion of treatment.

Another means of determining the extent of an acute phase response is by comparing the patient's baseline level of total plasma protein concentration with the level subsequent to IL-6 administration.

Changes in total plasma protein concentration can be monitored by the erythrocyte sedimentation rate (ESR), which is a qualitative measure of the density of the liquid portion of the blood.

Suppression or amelioration of the acute phase response by co-administering GM-CSF to subjects receiving IL-6 has been found to be achieved without apparent adverse effect on certain primary therapeutic functions of either cytokine, such as the activity of IL-6 in stimulating thrombocytopoiesis, or of the activity of GM-CSF to increase neutrophil production.

According to the method of the invention, a granulocyte macrophage colony stimulating factor is co-administered with the IL-6 cytokine.

By "co-administered" is meant administration of the total daily dosage of each respective cytokine within a common time period of no greater than 15 hours, preferably no greater than 8 hours or 4 hours, and more preferably, no greater than two hours. Desirably, the GM-CSF is administered within 2 hours or less of IL-6 administration, since the half-life of IL-6 in the body is about 2–4 hours. More desirably, the GM-CSF is administered within 1 hour down to 30 minutes, or even fifteen minutes of IL-6 administration. Optimally, the total daily dosage of both cytokines are administered simultaneously or virtually simultaneously.

If the daily dose of one or both cytokines is divided into smaller doses, then administration of the two cytokines may be made in any time order provided that the complete dose of each cytokine has been administered over a 15-hour period or lesser periods as described above.

A dosage regimen involved in a method for treating the previously mentioned conditions will be determined based on various factors affecting the action of drugs, e.g., body weight, sex and diet of the patient, severity of infection, time of administration, etc.

In general, the IL-6 will be administered in an amount effective to increase the platelet count of the patient. An effective daily dose of IL-6 for such purposes will range from 0.50 to 20 micrograms (μg) per kilogram of body weight expressed as non-glycosylated IL-6, more usually 1 to 8 mg/kg, and preferably 1.0 to 6 μg/kg. The more preferred effective amount of IL-6 usually ranges from 1.5 to 5.0 μg/kg/day. The amount of GM-CSF to be administered will be an amount effective to reduce the acute phase response of IL-6 and may be expressed as a weight ratio relative to the IL-6. In particular, the weight ratio of GM-CSF to IL-6 will be at least about 1:1 with both the GM-CSF and IL-6 being expressed as non-glycosylated protein-Increasing the weight ratio of GM-CSF to IL-6 above the 1:1 ratio may be used to further reduce the acute phase response. Hence, ratios up to about 8:1 or even greater may be used; such that the GM-CSF to IL-6 weight ratio may range from 1:1 to 8:1 or may be even a higher ratio. Preferably, the weight ratio of GM-CSF to IL-6 will be in the range of from 1:1 to 6:1, with very good results indicated at a ratio of 1:1 or somewhat higher, e.g., at least about 2:1 or in the range of from 1:1 to 5:1, both proteins being expressed as a non-glycosylated protein.

It is particularly preferred to also co-administer the GM-CSF in an amount sufficient to increase circulating neutrophils. For such purpose, the daily dosage of GM-CSF may range from 1 to 20 micrograms (μg) per kilogram of body weight, usually 1 to 10 μg/kg, preferably from 1.5 to 8 μg/kg/day and more preferably from 2 to 6 μg/kg/day, expressed as non-glycosylated GM-CSF.

An effective treatment with IL-6 to increase platelets will generally take place over several days, typically over a 4 to 21 day period which may be interrupted for a day or two, and which may be repeated after a few days interruption, depending upon the cause of the deficiency in platelets, for example, the periods of chemotherapy treatment.

Typically, the method of the invention will be carried out by administering to a patient a composition comprising the purified protein in conjunction with physiologically acceptable carriers, excipients or diluents such as neutral buffered saline, or saline mixed with serum albumin.

The compositions can be administered parenterally. Examples of parenteral administration include subcutaneous, intravenous, intra-arterial, intramuscular, and intraperitoneal, with subcutaneous being preferred.

For parenteral administration, the IL-6 and GM-CSF will generally be formulated in a unit dosage injectable form (solution, suspension, emulsion), preferably in a pharmaceutically acceptable carrier medium that is inherently non-toxic and non-therapeutic. Examples of such vehicles include without limitation saline, Ringer's solution, dextrose solution, mannitol and normal serum albumin. Neutral buffered saline or saline mixed with serum albumin are exemplary appropriate vehicles. Non-aqueous vehicles such as fixed oils and ethyl oleate may also be used. Additional additives include substances to enhance isotonicity and chemical stability, e.g., buffers, preservatives and surfactants, such as Polysorbate 80. The preparation of parenterally acceptable protein solutions of proper pH, isotonicity, stability, etc., is within the skill of the art.

Preferably, the product is formulated by known procedures as a lyophilizate using appropriate excipient solutions (e.g., sucrose) as a diluent.

The cytokines may be combined in vitro before administration to the patient, or alternatively, can be separately administered. While separate injections of IL-6 and GM-CSF are typically carried out, a single injection may be possible, provided the proteins may be suitably combined without loss of efficacy.

The therapy may be administered to mammals, particularly primates, including human and non-human primates, and especially humans.

EXAMPLES

Sources of Recombinant Cytokines rh IL-6 rhIL-6 was prepared from recombinant *E. coli* as a non-glycosylated, N-methionine terminated protein according to the method basically described in published PCT patent application WO 88/00206. The rhIL-6 that accumulated intracellularly was extracted from *E. coli* cells expressing IL-6 cDNA from a plasmid vector and purified to homogeneity by a series of chromatographic steps, including high-performance liquid chromatography (HPLC) and column chromatography. Sodium dodecyl sulfate-polyacrylamide gel electrophoresis (SDS-PAGE) demonstrated the presence of a single Coomassie blue staining band with a purity of greater than 98%. The specific activity was $9.2 \times 10^7$ U/mg protein, assayed using a modification of the mouse cell line B13.29 bioassay as described by Lansdorp et al., *Current Topics in Microbiology and Immunology*, Vol. 132, Springer-Verlag, 1986, 105–113. The endotoxin content was less than 0.1 Eu/ml as determined by the Limulus assay (Levin et al., Thomb. Diath. Haemorh 19:186 (1968), limulus amoebocyte lysate; Whittaker MA Bioproducts, Walkersville, Md.)

The IL-6 was formulated into a sodium phosphate buffered saline solution, containing Polysorbate 80, sucrose and glycine, pH about 7.5, and lyophilized. The lyophilizate was reconstituted for the subcutaneous treatment by thawing in water. The solutions had a specific activity of approximately $11.9 \times 10^7$ units/mg protein.

rhGM-CSF

Non-glycosylated, rhGM-CSF was obtained from recombinant *E. coli*, which method is basically described in published PCT patent application No. WO 86/00639. The crude protein extract was purified by anion exchange chromatography followed by gel filtration chromatography. The pooled fractions which constituted the purified GM-CSF were filtered and stored at $-80°$ C. The specific activity, as determined by bioassay and HPLC, was $2.63–3.29 \times 10^8$ U/mg protein.

In Vivo Administration of Cytokines

Animals

Fifteen young adult male rhesus monkeys, *Macaca mulatta*, approximately 4 years old, weighing between 3.5 and 6.3 kg., were housed individually in stainless steel squeeze cages in an air-conditioned room. The monkeys were fed Purina Certified Primate Chow and had access to food and water ad libitum. The temperature and humidity were maintained at $78\pm2°$ F. and $50\pm20\%$, respectively. Fresh fruit was given daily to supplement the routine food source.

The fifteen monkeys were randomly assigned to five groups containing 3 animals each.

Baseline Levels of Alpha-2-Macroglobulin and Fibrinogen

Figure 4:
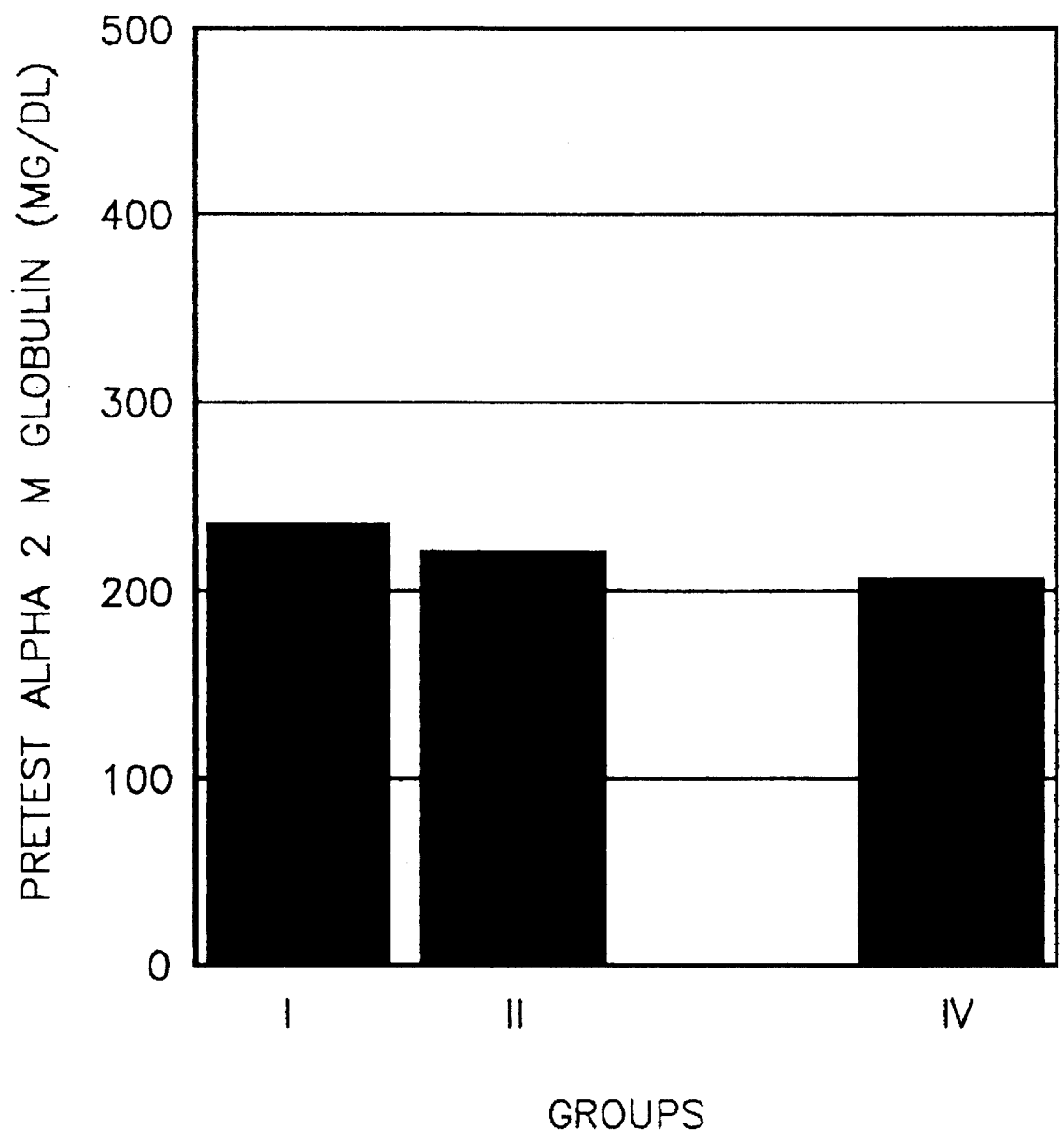
Figure 6:
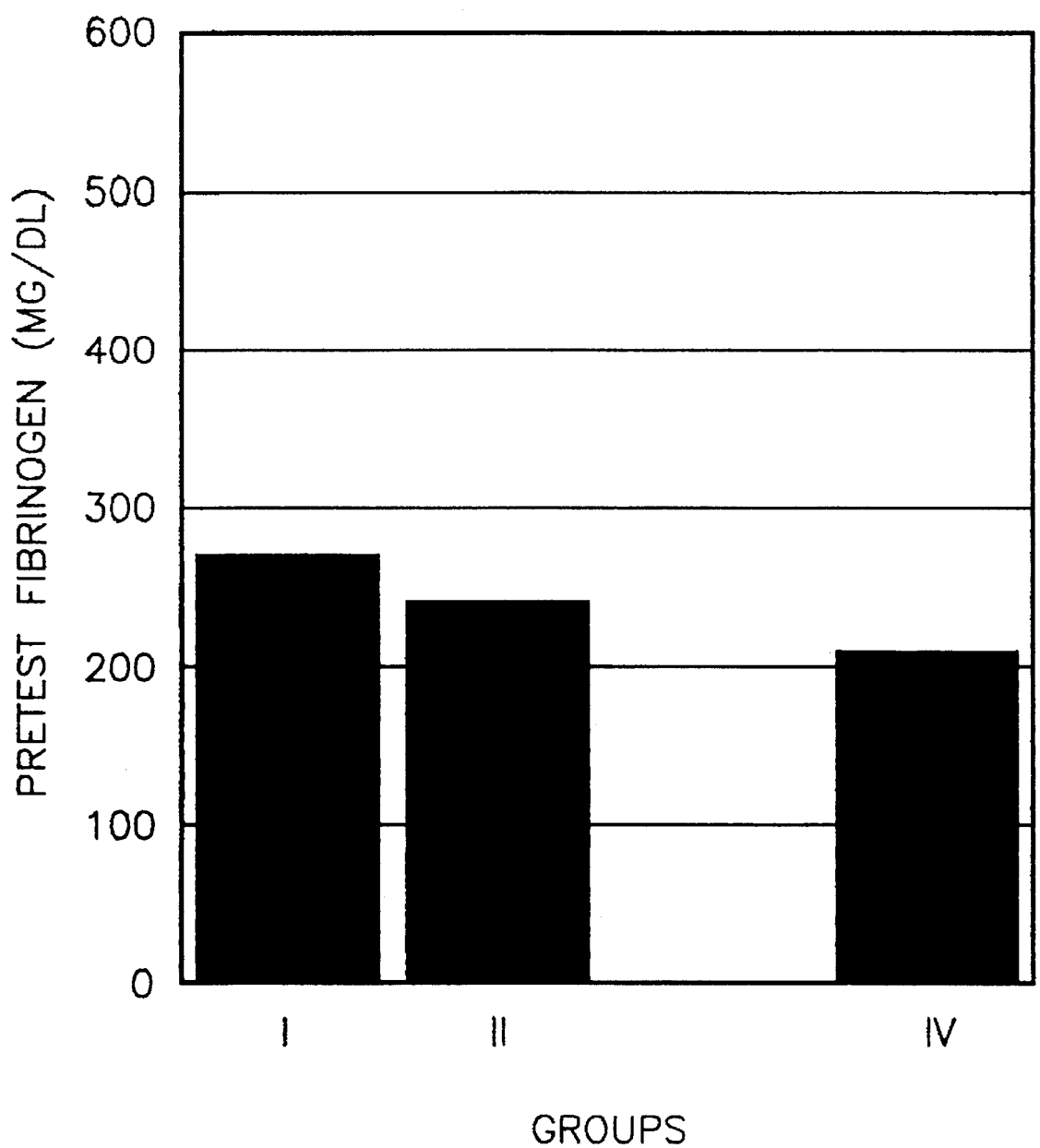

Alpha-2-macroglobulin and fibrinogen levels (mg/dl) of each test animal were taken to determine base level activity. The average base levels for each group of animals is graphically represented on FIGS. 4 and 6, respectively.

Testing Protocol

For a period lasting 30 or 31 days, each animal received a daily subcutaneous injection of IL-6 and/or Neupogen containing each cytokine in micrograms corresponding to the following dosages:

| Group | Dose of Cytokine (μg/kg/day) |
|---|---|
| Group I | 20 rhIL-6 |
| Group II | 20 rhGM-CSF |
| Group IV | 20 rhIL-6 + 20 rhGM-CSF |

Daily clinical observations and weekly body weights were recorded during weeks −3 to 5. Eye examinations were performed in weeks −3 and 5. Blood was withdrawn for clinical pathology and immunology determinations and testing for baseline levels of platelets, neutrophils, and acute phase proteins, in pretest weeks (FIGS. 1, 2, 4 and 6). Additional blood samples were withdrawn for hematology and immunology evaluations twice in week 1 and once in weeks 2, 3 and 4. On days 30 and 31 necropsy and macroscopic examinations of the tissues were performed. Tissue sections stained with hematoxylin and eosin were examined histologically from each animal. An oil red O section of the liver was examined from all animals on the study. Bone marrow brush smears were prepared at necropsy and evaluated.

Drug-related clinical signs were minimal, animals that received a combination of IL-6 and GM-CSF experiencing some edema at the injection site. One animal, of Group II, exhibited severe signs and had a 15% decrease in body weight, but these were determined to be unrelated to drug administration. This animal was not included in the data evaluation presenting for Group II, and accordingly these results represent data for two animals rather than three.) All other animals survived in good health for the duration of the study.

The following parameters were measured weekly over the duration of the study:

I. Determination of serum proteins of the acute phase response.
  (1) Alpha-2-macroglobulin count (mg/dl) was taken using a Boehringer Mannheim/Hitachi 717 analyzer and reagent available from Atlantic Antibodies.
  (2) Fibrinogen count (mg/dl) was monitored by an automated Fibrinogen Determination as described by Morse et al., *Amer. J. Clin. Path.* 55 671 (1971).

II. Platelet Count (thousand per milliliter blood) was determined using Coulter Counter Model "S-Plus"; see Coulter Counter Operator's Reference Manual #4201074F/Nov. 1979, Section III, pp. 3–9.

III. Differential Leukocyte Counts were determined using a manual method as described in the following: (1) Approved Laboratory Techinc, Kolmer, Spaulding, Robinson, Fifth Edition, 1959, p. 101; (2) Laboratory Medicine—Hematology, Miale, John B., Second Edition, 1962, p. 811.

IV. Erythrocyte Sedimentation Rate (ESR) was determined by the Wintrobe method of Wintrobe-Landsberg described in Gradwohl's Clinical Laboratory Methods and Diagnosis, Sixth Edition, Volume Two, p. 1151, see FIG. 3.

No macroscopic findings appeared related to cytokine administration. Microscopic observations that were drug related were limited to spleen, bone marrow and injection sites. A myeloid hyperplasia of the bone marrow which included an increase in neutrophils and eosinophils was detected in the animals which received the combination of IL-6+GM-CSF. Injection site reactions included hemorrhage and focal cellular infiltrates. It appeared that the doses of these cytokines alone and in combination were well tolerated in the non-human primate.

Discussion

Figure 2:
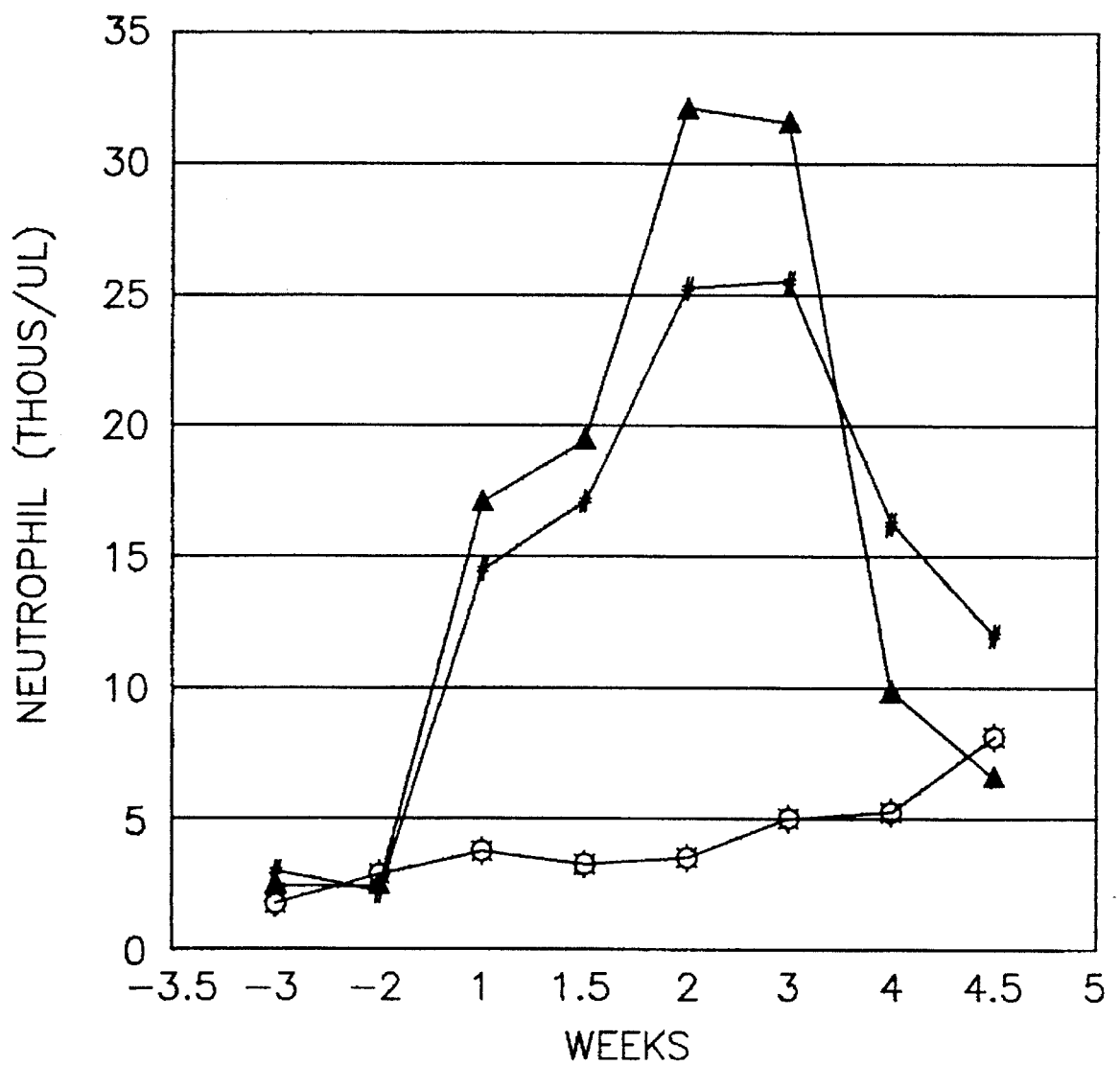
Figure 3:
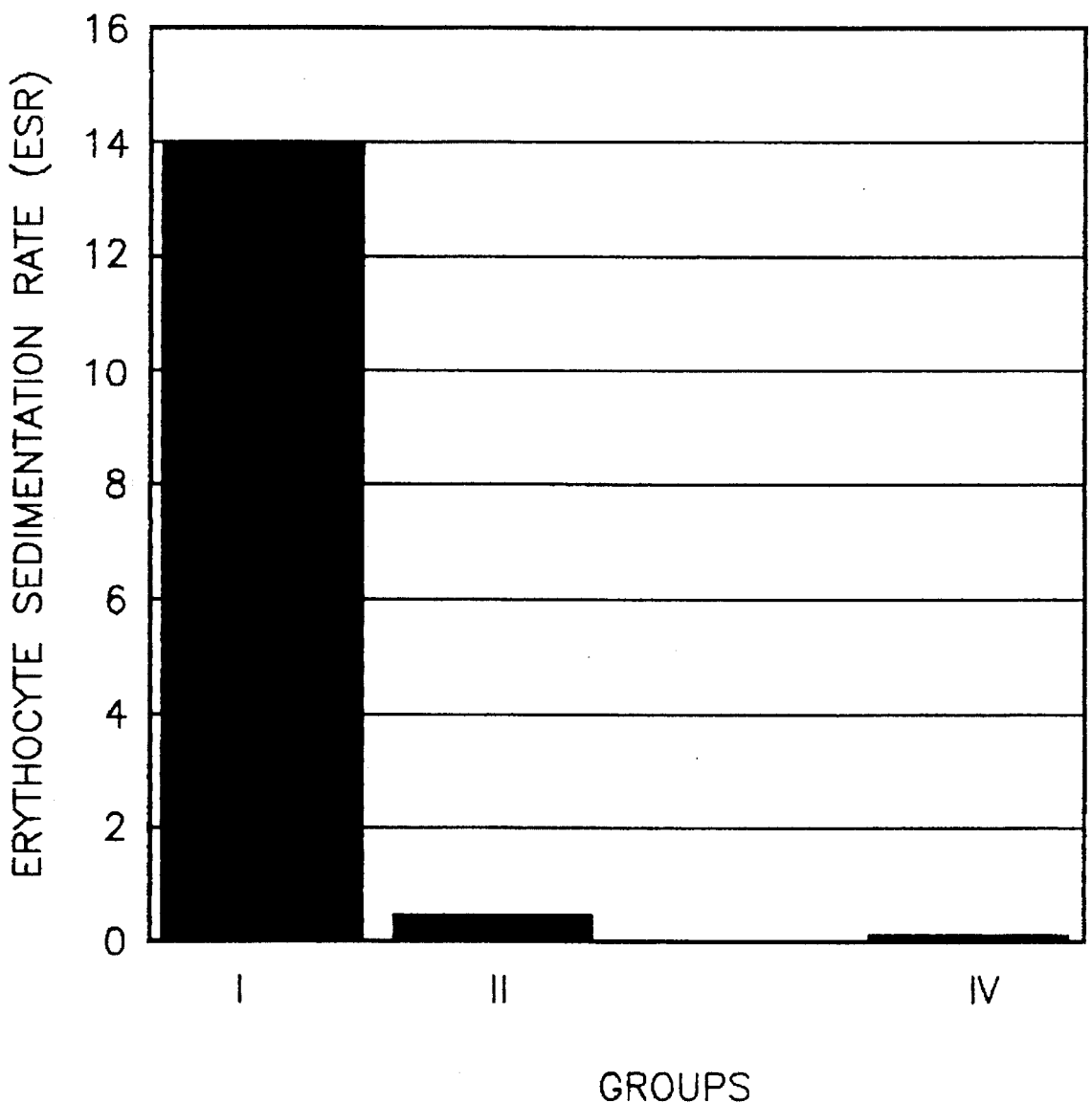
Figure 5:
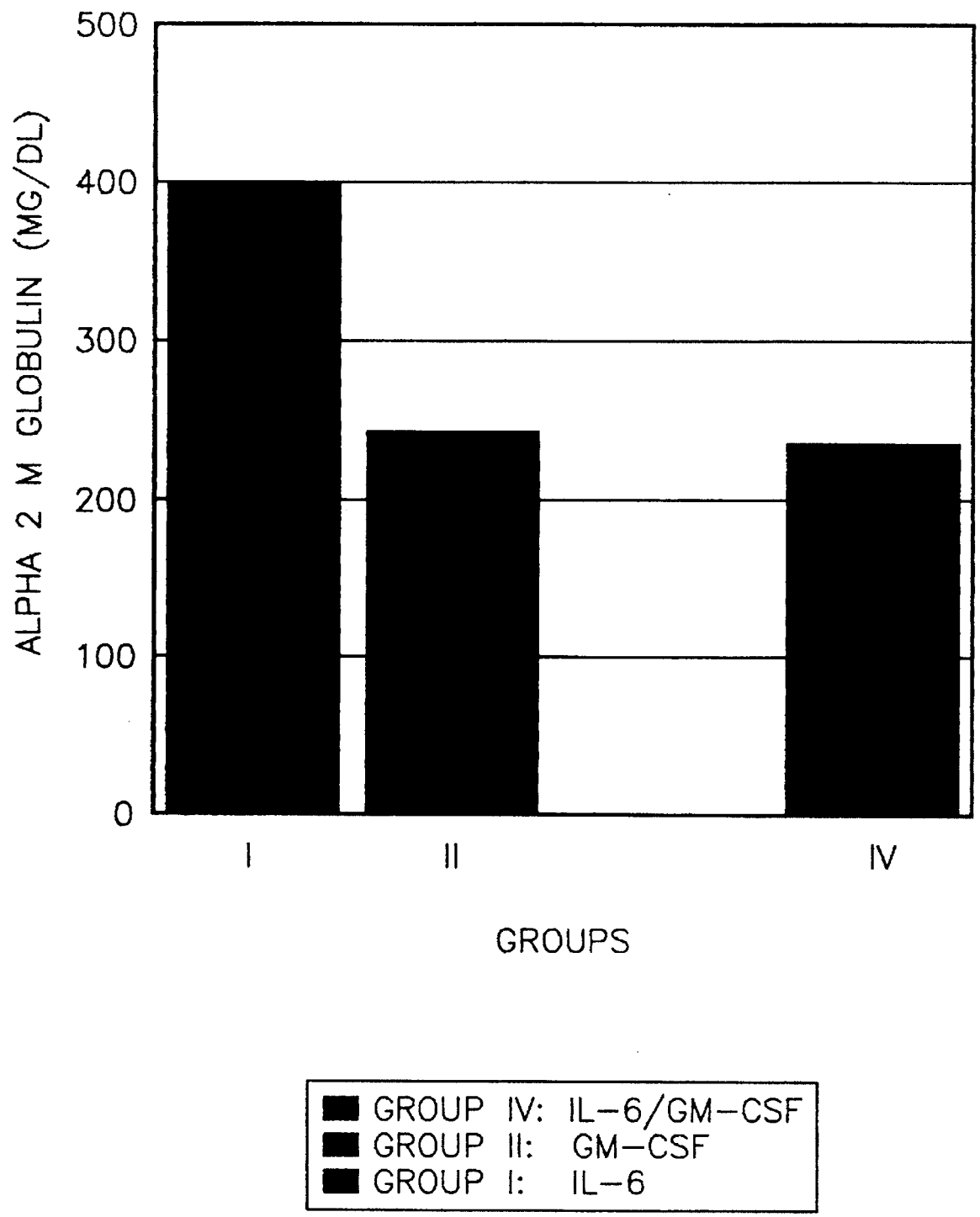
Figure 7:
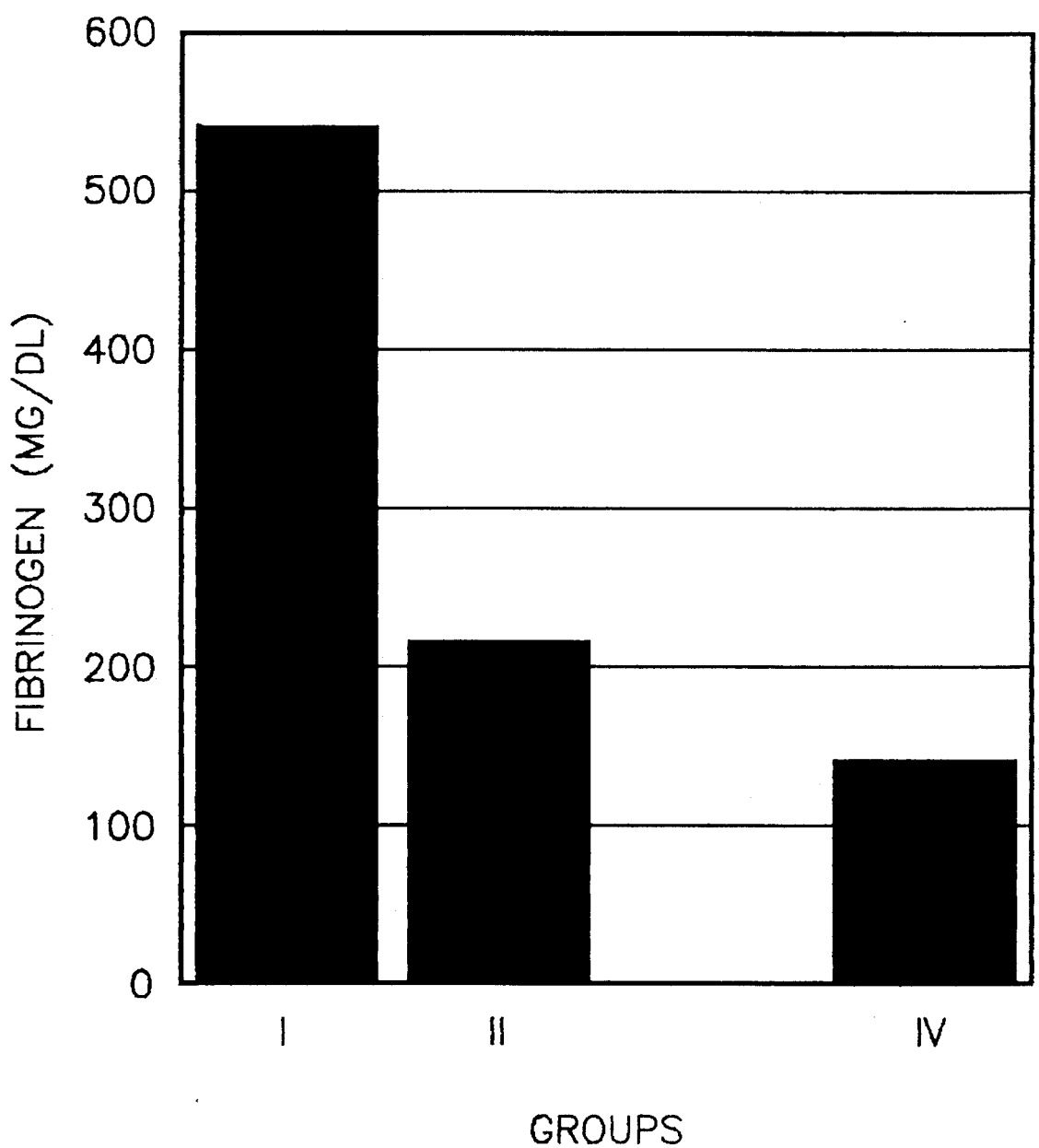

The pharmacological activities noted involved the hematopoietic system and the bone marrow. In general the effects were: IL-6 alone, augmentation of platelets (FIG. 1); GM-CSF alone an increase in neutrophils (FIG. 2) and the combination of IL-6 and GM-CSF an expansion of the platelets and neutrophils (FIGS. 1 and 2). IL-6 treatment alone clearly augmented blood proteins whereas the GM-CSF alone and the GM-CSF/IL-6 combination caused essentially no change (FIG. 3). The acute phase response (characterized by alterations in plasma proteins and alpha-2-macroglobulin levels) was clearly increased in the monkeys which received IL-6 alone (FIGS. 5 and 7), but was substantially reduced when the subjects were administered IL-6 with GM-CSF (FIGS. 5 and 7). No other clinical pathology parameters were significantly altered.

What is claimed is:

1. A method for treating the acute phase response in a patient receiving human IL-6 protein, which method comprises co-administering to the patient a platelet count increasing effective amount of human IL-6 protein and an acute phase response-suppressing effective amount of human GM-CSF protein, the weight ratio of such GM-CSF to such IL-6 being at least 1 to 1 expressed as non-glycosylated proteins, whereby the acute phase response is suppressed.

2. The method of claim 1 in which the human IL-6 protein is administered at a daily dose of from 1.0 to 6.0 micrograms, expressed as non-glycosylated protein, per kilogram of patient body weight.

3. The method of claim 2 in which the human GM-CSF protein is administered at a daily dose of from 2.0 to 6 micrograms, expressed as non-glycosylated protein, per kilogram of patient body weight and the weight ratio of juman GM-CSF plrotein to IL-6 is ant least 2 to 1.

4. The method of claim 1 in which the human GM-CSF protein is administered at a daily dose of from 1.5 to 8.0 micrograms, expressed as non-glycosylated protein, per kilogram of patient body weight.

5. The method of claim 1 in which the human IL-6 protein is administered at a daily dose of from 0.5 to 20 micrograms, expressed as non-glycosylated protein, per kilogram of patient body weight.

6. The method of claim 5 in which the human GM-CSF protein is administered at a daily dose of from 1.5 to 8 micrograms, expressed as non-glycosylated protein, per kilogram of patient body weight.

7. The method of claim 6 in which the weight ratio of human GM-CSF protein to human IL-6 protein is above 8:1 expressed as non-glycosylated protein.

8. The method of claim 6 in which the weight ratio of human GM-CSF protein to human IL-6 protein is 1:1 to 6:1 expressed as non-glycosylated protein.

9. The method of claim 6 in which the total daily dosage of both proteins is administered within a common time period of no greater than 15 hours.

10. The method of claim 6 in which the total daily dosage of both proteins is administered within a common time period of no greater than 4 hours.

11. The method of claim 1 in which the human GM-CSF protein is administered at a daily dosage of 1 to 20 micrograms, expressed as non-glycosylated protein, per kilogram of body weight.

12. The method of claim 11 in which the weight ratio of human GM-CSF protein to human IL-6 protein is from 1:1 to 5:1 expressed as non-glycosylated proteins.

13. The method of claim 12 in which the total daily dosage of both proteins is administered within a common time period of no greater than 8 hours.

14. The method of claim 12 in which the total daily dosage of both proteins is administered within a common time period of 2 hours or less.

15. The method of claim 1 in which the total daily dosage of both proteins is administered within a common time period of no greater than 15 hours.

16. The method of claim 1 in which the total daily dosage of both proteins is administered within a common time period of no greater than 8 hours.

17. The method of claim 1 in which the total daily dosage of both proteins is administered at the same time.

* * * * *